United States Patent [19]
Sharif et al.

[11] Patent Number: 5,517,261
[45] Date of Patent: May 14, 1996

[54] FOCUSING METHOD FOR A CORNEAL TOPOGRAPHER

[75] Inventors: Asif Sharif, Tustin, Calif.; Daniel R. Peters, Houston, Tex.; Keming Lu, Tustin, Calif.; Sami El Hage, Houston, Tex.

[73] Assignee: Alcon Laboratories, Inc., Fort Worth, Tex.

[21] Appl. No.: 354,294

[22] Filed: Dec. 13, 1994

[51] Int. Cl.⁶ .................................................. A61B 3/00
[52] U.S. Cl. ...................... 351/246; 351/206; 351/212; 351/247
[58] Field of Search .................... 351/246, 212, 351/247, 211, 205, 206, 209, 210; 354/62

[56] References Cited

U.S. PATENT DOCUMENTS

| | | | |
|---|---|---|---|
| 4,685,140 | 8/1987 | Mount, II | 382/6 |
| 4,772,115 | 9/1988 | Gersten et al. | 351/212 |
| 4,863,260 | 9/1989 | Gersten et al. | 351/212 |
| 4,902,123 | 2/1990 | Yoder, Jr. | 351/212 |
| 4,978,213 | 12/1990 | El Hage | 351/212 |
| 4,995,716 | 2/1991 | Warnicki et al. | 351/212 |
| 5,009,498 | 4/1991 | Gersten et al. | 351/212 |
| 5,062,702 | 11/1991 | Bille | 351/212 |
| 5,106,183 | 4/1992 | Yoder, Jr. | 351/212 |
| 5,159,361 | 10/1992 | Cambier et al. | 351/212 |
| 5,227,818 | 7/1993 | El Hage | 351/212 |
| 5,300,965 | 4/1994 | Kitajima | 351/212 |

OTHER PUBLICATIONS

Tomey, TMS-1 Topographic Modeling System, Tomey Technology, Inc., 1992.
Fundamentals of Corneal Topography, EyeSys Technologies, 1992.

*Primary Examiner*—William L. Sikes
*Assistant Examiner*—Hung Xuan Dang
*Attorney, Agent, or Firm*—Jeffrey S. Schira

[57] ABSTRACT

A method for focusing a corneal topographer by determining the maximum intensity of a reflected light during a first focusing sweep and capturing the topographic image during a second sweep when the reflection intensity reaches the maximum intensity.

6 Claims, 3 Drawing Sheets

FOCUSING METHOD FOR A CORNEAL TOPOGRAPHER

BACKGROUND OF THE INVENTION

This invention relates generally to the field of keratoscopic instruments and more particularly to corneal topographers.

In a number of ophthalmic surgical procedures it is desirable to have a three dimensional or topographic map of the cornea. In particular, corneal topographers can be extremely useful in conjunction with radial keratotomy surgery, phototherapeutic and photorefractive keratectomy procedures as well as in conjunction with contact lens fitting procedures.

Several corneal topographers are commercially available and each operates in basically the same manner. A series of concentric light rings are projected onto the cornea and are reflected back into the topographer, where the reflected ring pattern is captured electronically by a CCD camera and digitized. If the reflecting surface is perfectly spherical, the reflected ring pattern will be identical to the projected ring pattern. If the reflecting surface is aspherical, the reflected ring pattern will be distorted, and this distortion can be translated through a series of algorithms into a three dimension plot of the reflecting surface. The operation of ring pattern corneal topographers is more fully discussed in U.S. Pat. Nos. 4,685,140, 4,772,115, 4,863,260, 4,978,213, 4,995,716, 4,902,123, 5,009,498, 5,018,850, 5,062,702, 5,106,183, 5,159,361, 5,227,818 and 5,300,965 the entire contents of which are incorporated herein by reference. Other corneal topographers using reflected laser beam imaging systems are under development but not yet commercially available.

With ring pattern corneal topographers, the sharpness of the reflected ring pattern directly affects the accuracy of the topographic measurement because the reflected pattern is digitized prior to being electronically processed and an out of focus or fuzzy image may give an inaccurate reading or may not be intense enough to be perceived by the topographer electronics as a data point. Therefore, commercially available corneal topographers all contain a device to either automatically focus the light rings on the cornea or to assist the operator in manually focusing the light rings.

For example, the corneal topographer manufactured by Computed Anatomy and sold by Tomey uses two low powered aiming lasers that produce spots on the cornea. The laser are arranged so that when the spots precisely overlap, the topographer is in focus. Another topographer manufactured and sold by EyeSys Technologies, Inc. uses a crosshair sight that must be aligned within an illuminated target to ensure proper focus. Still another topographer, the EH-270, manufactured and sold by Alcon Laboratories, Inc., uses an LED and a stepper motor driven focusing system. The stepper motor moves the optical system along the optical axis to five known points where the intensity of the reflection of the LED off of the cornea is measured. Using a curve fitting algorithm, the topographer calculates the theoretical peak intensity and its location along the optical axis and the stepper motor moves the optical system back to this calculated "optimal" focus location. This method is more fully described in copending and commonly assigned U.S. Patent Application Ser. No. 08/046,619, filed Apr. 14, 1993, the entire contents of which is incorporated herein by reference.

While the focusing methods used by the topographers discussed above are accurate, triangulation-based methods such as aiming lasers and cross-hair sights require a certain degree of operator skill, and the LED/stepper motor method requires the use of a relatively precise (and expensive) mechanical positioning system.

Accordingly, a need continues to exist for a simple, inexpensive and precise method for focusing a corneal topographer.

BRIEF SUMMARY OF THE INVENTION

The present invention improves upon prior art corneal topographer focusing methods by providing a method that does not require triangulation alignment by an operator and does not require complex mechanisms for alignment. With the present method, an LED light source projects a target onto the cornea and the operator "sweeps" the topographer optics along the optical axis, gradually bringing the target (and necessarily the cornea) into focus and then slightly out of focus. During this first sweep, the intensity of the reflected LED light will gradually increase as the cornea is brought into focus, with the point of maximum intensity occurring when the cornea is in focus, and then gradually decrease as the cornea is brought out of focus. Once the maximum reflected LED light intensity is known, a second "sweep" is performed. When the LED light intensity reaches the maximum value, the concentric light rings are illuminated automatically and the reflection pattern of the light rings is captured by the CCD camera. This method results in the reflected light pattern being captured at the point of optimal focus without the use of any complex mechanism by an operator that need not be highly trained.

Accordingly, one objective of the present invention is to provide a method of focusing a corneal topographer that does not require complex mechanisms.

Another objective of the present invention is to provide a method of focusing a corneal topographer that tracks the intensity of a target light source and automatically captures the image to be analyzed at the point of maximum intensity.

Still another objective of the present invention is to provide a method of focusing a corneal topographer that minimizes operator error.

Yet another objective of the present invention is to provide a method of focusing a corneal topographer that minimizes operator involvement.

These and other objectives and advantages of the present invention will become apparent from the detailed description, drawings and claims that follow.

DETAILED DESCRIPTION OF THE INVENTION

While the present method may be implemented in any of the corneal topographers described in the patents listed above, topographers having a frusto conical optics head such as those described in U.S. Pat. Nos. 4,978,213 and 5,227,818 are preferred. As the corneal topographer itself does not form a part of the present invention, a detailed description of the topographer mechanism will not be given. The present invention may be implemented through the appropriate commands in the topographer operating software.

Figure 1:
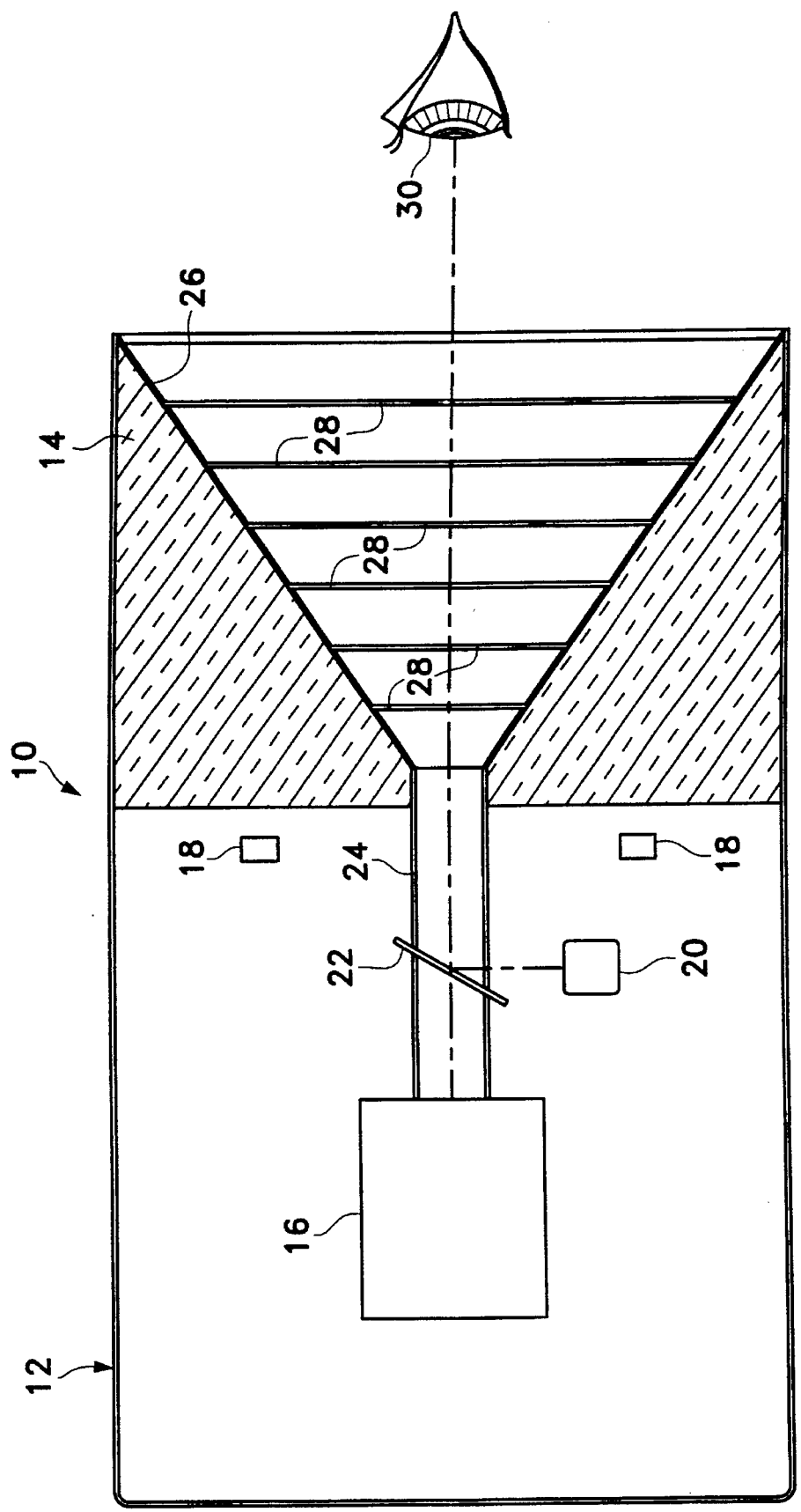
FIG. 1 is a cross sectional view of the optics head of a corneal topographer suitable for practicing the method of the present invention.

As seen in FIG. 1, optics head 10 of a corneal topographer suitable for practicing the present invention generally consists of housing 12, target 14, CCD camera 16, lights 18, light-emitting diode (LED) 20, partial reflector 22 and light tube 24. Target 14 preferably is made from a transparent material with the interior surface 26 covered with an opaque coating into which annular grooves 28 are cut. When lights 18 are illuminated, the light passes through transparent target 14 and grooves 28 to project a pattern of concentric light rings onto cornea 30. This light ring pattern is reflected off of cornea 30 and through tube 24 and is captured by CCD camera 16. During focusing, LED 20 is illuminated and directed onto cornea 30 by reflector 22.

Figure 2:
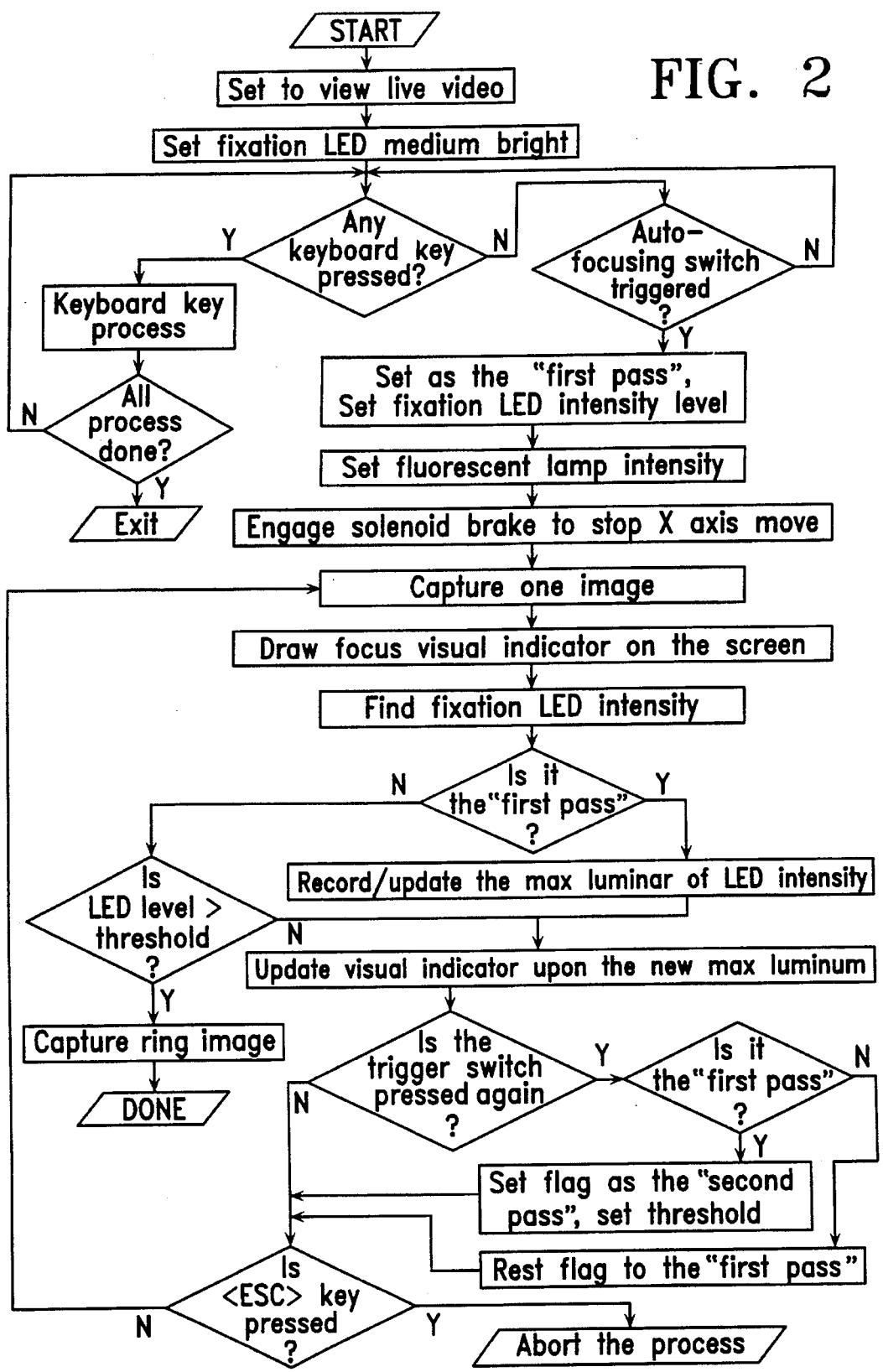
FIG. 2 is a flowchart illustrating the software commands suitable for implementing the method of the present invention.
Figure 3:
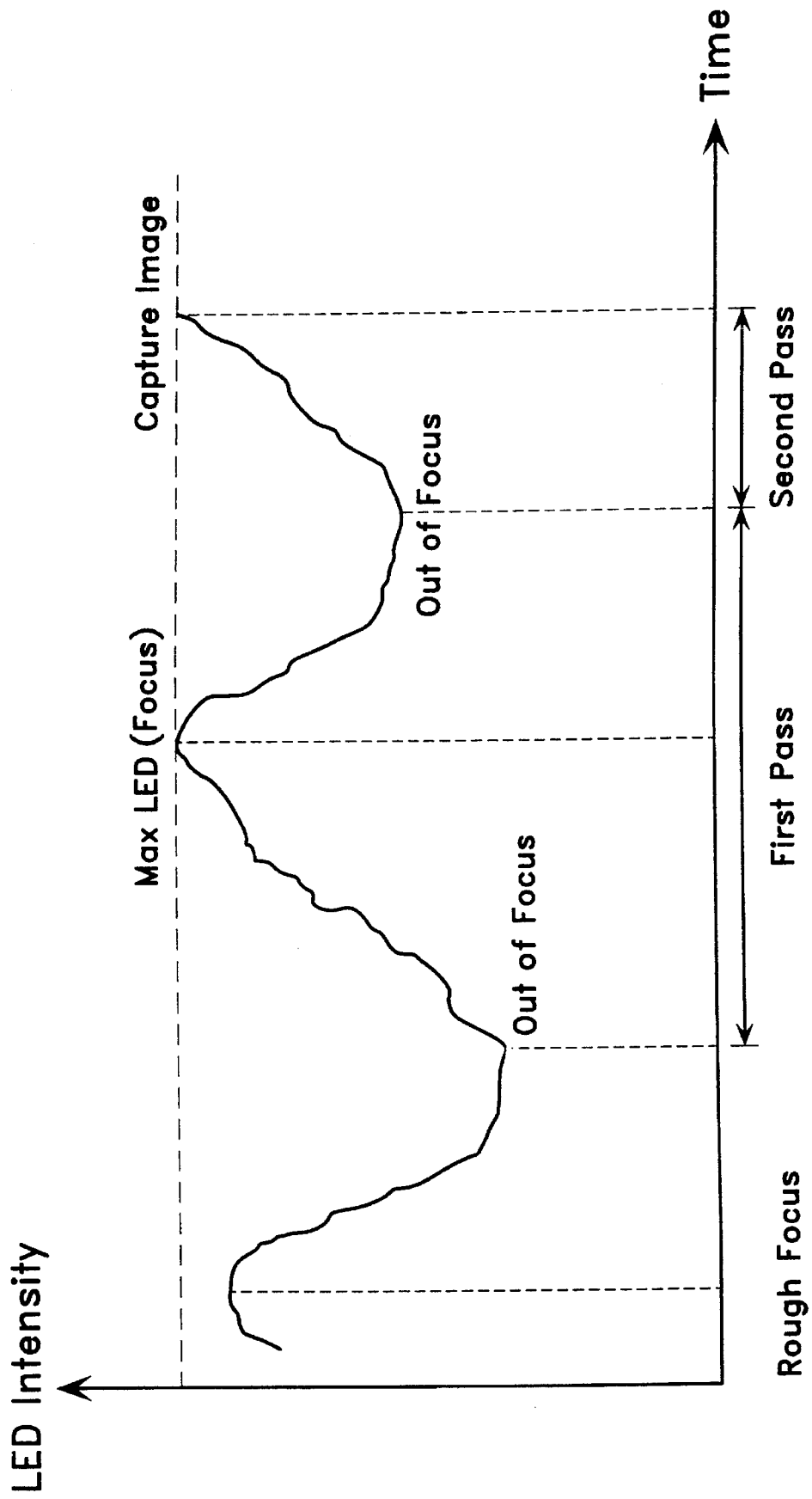
FIG. 3 is a plot of LED intensity versus time as the reflected LED light is brought into and out of focus using the method of the present invention.

As diagrammed in FIG. 2, the present focusing method is initiated by illuminating LED 20. The reflection of LED 20 is reflected off of cornea 30 and captured by CCD camera 16. The reflected image of LED 20 is digitized and the intensity of the image is measured by methods well-known in the art. A first focusing pass is performed by slowing adjusting the optics so that the reflection of LED 20 off of cornea 30 is brought into focus and continued until the reflection is slightly out of focus. During this first pass, it is not necessary for the operator to try to identify the point of optimal focus. Instead, the operator simply adjusts the optics so that the reflected image becomes more in focus, and then slightly out of focus. The digitized image of the reflection of LED 20 is sampled at a rate of 30 times per second and the intensity plotted as a function of time. An example of such a plot is illustrated in FIG. 3. As the reflection is brought into focus, the intensity level of the reflected image increases to a point of maximum intensity corresponding to the optimal focus. This maximum intensity level is stored by the topographer for use during the second pass.

Once the first pass is completed and the maximum intensity of the reflection of LED 20 off of cornea 30 is stored, the operator begins a second pass identical to the first pass by slowly bringing the reflection into focus. During the second pass, the intensity of the reflection of LED 20 is compared to the maximum intensity level obtained and stored during the first pass. When the LED intensity during the second pass reaches this maximum level, cornea 30 is in optimal focus. This triggers topographer to illuminate lights 18 so that the necessary ring pattern is reflected off of cornea 30 and the image is captured by CCD camera 16 for further topographic analysis by the topographer.

The above example is meant to be illustrative only. It will be apparent to those skilled in the art that changes or modification may be made to the invention as describe above without departing from its scope or spirit.

We claim:

1. A method for focusing a corneal topographer, comprising the steps of:

a. reflecting a light off of a cornea;

b. adjusting the topographer so that a reflection of the light is first brought into focus and subsequently out of focus;

c. measuring an intensity of the reflection of the light while the reflection of the light is brought into and out of focus;

d. determining a maximum intensity of the reflection of the light;

e. adjusting the topographer a second time so that the reflection of the light is brought back into focus;

f. reflecting a concentric ring pattern off of the cornea when the maximum intensity is reached during the second time the reflection of the light is brought into focus; and g. capturing the reflection of the concentric ring pattern.

2. The method of claim 1 wherein the light is a light-emitting diode.

3. The method of claim 1 wherein the reflection of the concentric ring pattern is captured by a CCD camera.

4. The method of claim 1 wherein the concentric ring pattern is formed by the illumination of a transparent target having a frusto conically shaped opening.

5. A method for focusing a corneal topographer, comprising the steps of:

a. reflecting a light from a light emitting diode off of a cornea;

b. adjusting the topographer so that a reflection of the light is first brought into focus and subsequently out of focus;

c. measuring an intensity of the reflection of the light while the reflection of the light is brought into and out of focus;

d. determining a maximum intensity of the reflection of the light;

e. adjusting the topographer a second time so that the reflection of the light is brought back into focus;

f. reflecting a concentric ring pattern off of the cornea when the maximum intensity is reached during the second time the reflection of the light is brought into focus; and g. capturing the reflection of the concentric ring pattern with a CCD camera.

6. The method of claim 5 wherein the concentric ring pattern is formed by the illumination of a transparent target having a frusto conically shaped opening.

\* \* \* \* \*